(12) United States Patent
Weyer et al.

(10) Patent No.: US 6,262,300 B1
(45) Date of Patent: Jul. 17, 2001

(54) METHOD FOR PRODUCING CHLOROCARBOXYLIC ACID CHLORIDES

(75) Inventors: Hans-Jürgen Weyer, Bobenheim-Roxheim; Armin Stamm, Mainz; Theodor Weber, Ludwigshafen; Jochem Henkelmann, Mannheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/529,811

(22) PCT Filed: Nov. 21, 1998

(86) PCT No.: PCT/EP98/07500

§ 371 Date: Apr. 20, 2000

§ 102(e) Date: Apr. 20, 2000

(87) PCT Pub. No.: WO99/29648

PCT Pub. Date: Jun. 17, 1999

(30) Foreign Application Priority Data

Dec. 4, 1997 (DE) .............................. 197 53 773

(51) Int. Cl.⁷ .................................. C07C 51/58
(52) U.S. Cl. .................. 562/857; 562/856; 562/854; 562/828
(58) Field of Search .................. 562/857, 856, 562/828, 854

(56) References Cited

U.S. PATENT DOCUMENTS

| | | |
|---|---|---|
| 2,778,852 | 1/1957 | Adam . |
| 3,418,365 | 12/1968 | Gustafson . |
| 4,129,595 * | 12/1978 | Suzuki . |
| 4,764,309 * | 8/1988 | Decker et al. . |
| 5,130,478 | 7/1992 | Gauthier . |
| 5,430,186 * | 7/1995 | Ksoll et al. .................. 562/857 |
| 5,750,779 * | 5/1998 | Nagata et al. ................ 562/828 |
| 5,764,309 | 6/1998 | Krishnamurthy . |

FOREIGN PATENT DOCUMENTS

| | | |
|---|---|---|
| 36 24 258 | 1/1988 | (DE) . |
| 413 264 | 2/1991 | (EP) . |
| 435 714 | 7/1991 | (EP) . |

OTHER PUBLICATIONS

Chem.Abst.XP–002099244.

Houben Weyl, Meth.Chem.1983,Band 4,355–391;484–505.

* cited by examiner

Primary Examiner—Gary Geist
Assistant Examiner—Devesh Khare
(74) Attorney, Agent, or Firm—Keil & Weinkauf

(57) ABSTRACT

The present invention provides process for the preparation of chlorocarbonyl chlorides of the formula I $$R_1\text{—CHCl—Y—COCl} \qquad (I),$$

where $R^1$ is for example hydrogen or $C_1$- to $C_{20}$-alkyl and

Y is for example a saturated or mono- or polyolefinically unsaturated $C_2$–$C_8$-alkylene chain, by reacting lactones with a chlorinating agent in the presence of a urea compound.

6 Claims, No Drawings

METHOD FOR PRODUCING CHLOROCARBOXYLIC ACID CHLORIDES

The present invention relates to a novel process for preparing chlorocarbonyl chlorides by reacting lactones with chlorinating agents in the presence of urea compounds.

Chlorocarbonyl chlorides are known useful intermediates for organic syntheses, in particular of crop protection agents and drugs.

DE-A 36 24 258 discloses the preparation of chlorocarbonyl chlorides by reacting the corresponding lactones with phosgene in the presence of quaternary ammonium salts as catalysts. Although good yields are obtained by using this process, it leaves something to be desired from an industrial point of view, since the quaternary ammonium salts are insoluble both in the lactones and in the chlorocarbonyl chlorides, which makes work-up of the reaction mixture and in particular a continuous operation of the process difficult.

EP-A 413 264 and EP-A 435 714 describe a process for preparing chlorocarbonyl chlorides by chlorination of lactones using phosgene in the presence of phosphine oxides where phosphorus-containing distillation residues are obtained whose disposal is complicated by the formation of phosphoric acid during the incineration of the residues. Furthermore, U.S. Pat. No. 341 8 365 discloses a process for preparing chlorocarbonyl chlorides from lactones using thionyl chloride, however, this process gives only unsatisfactory yields.

It is an object of the present invention to provide a process for preparing chlorocarbonyl chlorides by reacting lactones with chlorinating agents; which avoids the disadvantages of the prior art processes.

We have found that this object is achieved according to the invention by a process for preparing of chlorocarbonyl chlorides of the formula I $$R^1\text{—CHCl—Y—COCl} \qquad (I),$$

where $R^1$ is hydrogen, or is $C_1$- to $C_{20}$-alkyl, $C_2$- to $C_{12}$-alkenyl, $C_2$- to $C_{12}$-alkynyl, each of which is unsubstituted or mono- to trisubstituted by $C_1$- to $C_4$-alkoxy, $C_2$- to $C_4$-acyl, $C_2$- to $C_4$-acyloxy, $C_2$- to $C_8$-dialkylamino, halogen, nitro and/or cyano, or is $C_3$- to $C_{12}$-cycloalkyl, $C_4$- to $C_{12}$-alkylcycloalkyl, $C_4$- to $C_{12}$-cycloalkylalkyl, heterocycloalkyl, $C_5$- to $C_{20}$-heterocycloalkylalkyl, $C_6$- to $C_{14}$-aryl, $C_7$- to $C_{20}$-arylalkyl or $C_7$- to $C_{20}$-alkylaryl, each of which is unsubstituted or mono- to trisubstituted by $C_1$- to $C_4$-alkyl, $C_1$- to $C_4$-alkoxy, $C_2$- to $C_4$-acyl, $C_2$- to $C_4$-acyloxy, $C_2$- to $C_8$-dialkylamino, halogen, nitro and/or cyano, and Y is a saturated or mono- or polyolefinically unsaturated $C_2$–$C_8$-alkylene chain which may be interrupted by an ether, thioether, tertiary amino, keto, lactone, N-alkylsubstituted lactam or sulfone group and is unsubstituted or mono- to trisubstituted by $C_1$- to $C_{12}$-alkyl, $C_1$- to $C_8$-alkoxy, $C_2$-$C_4$-acyl, $C_2$-$C_4$-acyloxy, $C_2$-$C_8$-dialkylamino, halogen, nitro and cyano, by reacting the lactone of the formula II

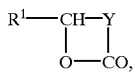

(II)

where $R^1$ and Y are each as defined above, with a chlorinating agent in the presence of a urea compound of the formula III $$R^2R^3N\text{—CX—}NR^4R^5 \qquad (III),$$

where the radicals $R^2$, $R^3$, $R^4$ and $R^5$ may be identical or different and, independently of the others, each has the meanings given for $R^1$ with the exception of hydrogen, or where one of the radicals $R^2$ or $R^3$ together with one of the radicals $R^4$ or $R^5$ are a hydrocarbon chain having 2 to 8 carbon atoms which may contain an ether, thioether, tertiary amino, keto, lactone, alkyl-substituted lactam, sulfone or diketo group and which is saturated or mono-or polyolefinically unsaturated and is unsubstituted or mono- to trisubstituted by $C_1$–$C_4$-alkyl, $C_1$–$C_4$-alkoxy, $C_2$–$C_4$-acyl, $C_2$–$C_4$-acyloxy, phenoxy, $C_2$–$C_8$-dialkylamino, halogen, nitro and cyano, or are a cycloalkylene group having 5 to 12 carbon atoms, a heterocycloalkylene group having 4 to 11 carbon atoms, an arylene group having 6 to 12 carbon atoms or a heteroarylene group having 3 to 11 carbon atoms, each of which is unsubstituted or mono- to trisubstituted by $C_1$–$C_4$-alkyl, $C_1$–$C_4$-alkoxy, phenoxy, $C_2$–$C_4$-acyl, $C_2$–$C_4$-acyloxy, $C_2$–$C_8$-dialkylamino, halogen, nitro and/or cyano, and where X is an oxygen or sulfur atom, and/or a urea compound of the formula IV

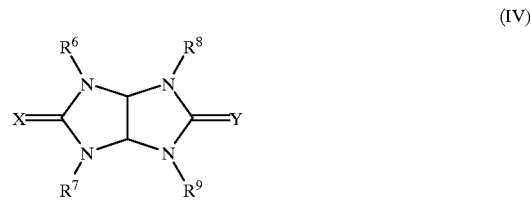

(IV)

where X is as defined above, $R^6$, $R^7$, $R^8$ and $R^9$ may be identical or different and, independently of the others, each has the meanings given for $R^1$, with the exception of hydrogen, and/or a compound of the formula (V),

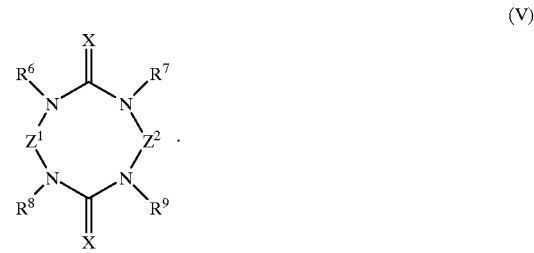

(V)

where X, $R^6$ to $R^9$ are each as defined above and $Z^1$, $Z^2$, which may be identical or different, are a methylene, ethylene or vinylene group which is unsubstituted or mono- to trisubstituted by $C_1$–$C_4$-alkyl, $C_1$–$C_4$-alkoxy, $C_2$–$C_4$-acyl, $C_2$–$C_4$-acyloxy, phenoxy, $C_2$–$C_8$-dialkylamino, halogen, nitro and/or cyano.

Y is a $C_2$–$C_8$-alkylene chain which may be interrupted by hetero atoms such as oxygen or sulfur or by groups which are inert to the chlorinating agent under the reaction conditions, for example a tertiary amino, keto, lactone, N-alkyl-substituted lactam or sulfone group. Y may furthermore be mono- to trisubstituted by groups which are inert to the chlorinating agent under the reaction conditions, for example by $C_1$–$C_4$-alkyl, $C_1$–$C_4$-alkoxy, $C_2$–$C_4$-acyl, $C_2$–$C_4$-acoxy, $C_2$–$C_8$-dialkylamino, halogen, nitro and cyano. Preferably, Y contains only carbon atoms as building blocks of the chain,, and no further substituents. Y is particularly preferably $C_2$–$C_4$-alkylene such as ethylene, propylene and butylene, in particular ethylene and propylene.

Independently of one another, the organic substituents RI to $R^9$ in the compounds I, II, III, IV and V have the following meanings:

$C_1$- to $C_{20}$-alkyl, preferably $C_1$- to $C_{12}$-alkyl, particularly preferably $C_1$- to $C_8$-alkyl such as methyl, ethyl, n-propyl, isopropyl, n-butyl, isobutyl, sec-butyl, tert-butyl, n-pentyl, isopentyl, n-hexyl, isohexyl, n-heptyl, isoheptyl, n-octyl and isooctyl, in particular $C_1$- to $C_4$-alkyl such as methyl, ethyl, n-propyl, isopropyl, n-butyl, isobutyl, sec-butyl and tert-butyl, $C_1$-$Cl_2$-alkenyl, preferably $C_2$-$C_8$-alkenyl, such as vinyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethylpropenyl, 1-ethyl-1-propenyl, 1-ethyl-2-propenyl, 1-hexenyl, 2-hexenyl, 3-hexenyl, 4-hexenyl, 5-hexenyl, particularly preferably vinyl, 2-propenyl and 1-butenyl, $C_1$- to $C_{12}$-alkynyl, preferably $C_2$–$C_8$-alkynyl, such as ethynyl, 1-propynyl, 2-propynyl, 1-butynyl, 3-butynyl, 1-methyl-2-propynyl, 1-pentynyl, 2-pentynyl, 3-pentynyl, 1-methyl-2-butynyl, l-methyl-3-butynyl, 2-methyl-3-butynyl, 3-methyl-1-butynyl, 1,1-dirmethyl-2-propynyl, l-ethyl-2-propynyl, 1-hexynyl, 2-hexynyl, 3-hexynyl, 4-hexynyl, 5-hexynyl, particularly preferably ethynyl, 1-propynyl and 1-butynyl.

The abovementioned groups may be substituted by $C_1$–$C_4$-alkoxy, $C_2$–$C_4$-acyl, $C_2$–$C_4$-acyloxy, $C_2$–$C_8$-dialkylamino, halogen, nitro and/or cyano. Preference is given to substituted alkyl radicals, particularly preferably halogen- or cyano-substituted alkyl radicals such as cyanomethyl, chloromethyl.

Furthermore, $R^1$ to $R^9$ are:

$C_3$- to $C_{12}$-cycloalkyl, preferably $C_5$- to $C_8$-cycloalkyl such as cyclopentyl, cyclohexyl, cycloheptyl and cyclooctyl, particularly preferably cyclopentyl and cyclohexyl, $C_4$- to $C_{12}$-alkylcycloalkyl, preferably $C_5$- to $C_{10}$-alkylcycloalkyl, particularly preferably $C_5$- to $C_8$-alkylcycloalkyl, $C_4$- to $C_{12}$-cycloalkylalkyl, preferably $C_5$- to $C_{10}$-cycloalkylalkyl, particularly preferably $C_5$- to $C_8$-cycloalkylalkyl, $C_5$- to $C_{20}$-alkylcycloalkylalkyl, preferably $C_6$- to $C_{16}$-alkylcycloalkylalkyl, particularly preferably $C_7$- to $C_{12}$-alkylcycloalkylalkyl, heterocycloalkyl, such as a 5- or 6-membered ring having one or two O, N and/or S atoms in the ring, which may be aromatic or nonaromatic, such as 2- or 3-furyl, 2- or 3-thienyl, 2- or 3-pyrrolyl, 2- or 4-imidazolyl, 2- or 3-oxazolyl, 2- or 3-oxazolyl, 2- or 3-thiazolyl, pyridinyl, morpholinyl, thiomorpholinyl and pyrazolyl, $C_6$- to $C_{14}$-aryl such as phenyl, 1-naphthyl and 2-naphthyl, preferably phenyl, $C_7$- to $C_{20}$-alkylaryl, preferably $C_7$- to $C_{16}$-alkylaryl, preferably $C_7$- to $C_{12}$-alkylphenyl such as 2-methylphenyl, 3-methylphenyl, 4-methylphenyl, 2-ethylphenyl, 3-ethylphenyl and 4-ethylphenyl, $C_7$- to $C_{20}$-arylalkyl, preferably $C_7$- to $C_{16}$-aralkyl, preferably $C_7$- to $C_{12}$-phenalkyl such as benzyl, 1-phenylethyl, 2-phenylethyl, 3-phenylpropyl, 1-phenylbutyl, 2-phenylbutyl, 3-phenylbutyl, 4-phenylbutyl, particularly preferably benzyl, 1-phenylethyl and 2-phenylethyl.

Furthermore, the radicals $R^2$ or $R^3$, together with one of the radicals $R^4$ or $R^5$, may be a cycloalkylene group having 5 to 12 carbon atoms which may be attached via vicinal carbon atoms or in 1,3 position. Examples include 1,2- or 1,3-cyclopentylene, 1,2-or 1,3-cyclohexylene and 1,2- or 1,3-cycloheptylene. The cycloalkylene group may also contain one or more hetero atoms such as nitrogen, oxygen or sulfur in place of one or more carbon atoms. Furthermore, the radicals $R^2$ or $R^3$, together with one of the radicals $R^4$ or $R^5$, may be a (divalent) arylene group having 6 to 12 carbon atoms which is attached via vicinal carbon atoms. Examples include ortho-phenylene, 1,2- or 2,3-naphthylene, and 1,2- or 2,3-anthracenylene, preferably ortho-phenylene. The arylene group may also contain one or more hetero atoms such as nitrogen in place of one or more carbon atoms. Examples include 2,3- or 3,4-pyrrolylene, 2,3- or 3,4-pyridinylene, 2,3-, 3,4-, 5,6- or 6,7-quinolinylene or 2,3-, 5,6- or 6,7-quinoxalinylene.

Preferred urea compounds of the formula III are those which are liquid under the reaction conditions, particularly preferably N,N'-dimethylethyleneurea, N,N'-dimethylpropyleneurea, N,N'-tetrabutylurea,, N,N'-tetramethylthiourea, N-chloromethyl-N'-cyanomethylpropyleneurea, N-methyl-N'-ethylpropyleneurea, 1,3-dimethyl-1,3-dihydrobenzimidazol-2-one, 1-methyl-3-phenylim:idazolidine-2,4,5-trione, 1,3,4,6-tetramethyl-1,3,4,6-tetrahydroimidazo[4,5-D]imidazole-2,5-dione and 4-methoxy-l-methyl-3-phenylimidazolidine-2-thione.

The abovementioned urea compounds may be used as such or in the form of their salts with hydrohalic acids, for example as hydrochlorides, or in the form of their salts which are obtainable by reaction with phosgene (Vilsmeier salts), preference being given to the hydrochlorides.

The urea compounds of the formula III, IV and V are obtainable for example by the reactions described in Houben-Weyl, Methoden der organischen Chemie, (1983) Volume E 4, pages 335–391 and pages 484–505.

The urea compounds of the formula III, IV and/or V are employed in a molar ratio of from 0.001:1 to 0.2:1, preferably 0.002:1 to 0.1:1, particularly preferably 0.005:1 to 0.05:1, relative to the lactone II.

The starting materials II which should be particularly mentioned, with respect to the importance of the process products I, are the unsubstituted lactones, ie. the butyrolactone, the valerolactone and the caprolactone.

If liquid lactones of a low melting point are employed, the reaction can generally be carried out without solvent. Otherwise, it is recommended to carry out the reaction in an inert solvent. Suitable solvents include high-boiling hydrocarbons such as cumene, toluene, xylene, benzene, or aromatic chlorine compounds such as chlorobenzene or dichlorobenzene, or else preferably the process product in amounts of up to 50% by weight, based on the lactone II.

Suitable for use as chlorinating agents are reagents which are known per se, such as phosgene, thionyl chloride, oxalyl chloride, and phosphorus trichloride, preference being given to the use of phosgene. The molar ratio of the chlorinating agent to the lactone II is from 0.5:1 to 50:1, preferably 1:1 to 2:1, particularly preferably 1:1 to 1.5:1 and very particularly preferably 1:1 to 1.2:1

Frequently, the concomitant use of hydrogen chloride is advantageous, namely in amounts of from 5 to 100 mol %, preferably 20 to 40 mol %, of lactone II. In the process according to the invention, the lactone II is reacted in the presence of the urea compound III, IV or V at from −20 to 180° C., preferably 0 to 120° C., particularly preferably 40 to 100° C., and at pressures of from 0.01 to 50 bar, preferably 0.5 to 5 bar, particularly preferably 0.9 to 1 bar, very particularly preferably at atmospheric pressure.

If the reaction is carried out batchwise, it is recommended to prepare a solution of lactone and urea compound and, if appropriate, the solvent and to introduce the chlorinating agent into this solution at the rate of its consumption. This way, from 1 to 3 mol of chlorinating agent per mole of lactone II are sufficient. The excess of chlorinating agent can be recycled into the reaction vessels in customary manner.

The advantages of the process according to the invention are particularly evident when the process is carried out continuously, either using a series of stirred tanks, a reaction column in countercurrent operation, a loop reactor, a reaction tube or a combination of the abovementioned reactors.

Work-up of the reaction mixture is carried out in a manner known per se, ie. generally by distillation, where prior to the distillation, if the chlorinating agent used is phosgene, excess phosgene may be removed, if desired.

It is an advantage of the process according to the invention that the reaction proceeds completely and selectively under relatively mild conditions, with low amounts of the urea compound. The reaction product can be worked up by customary methods for work-up, without the accumulation of phosphorus-containing residues, and the process can be carried out continuously.

The invention is illustrated in more detail by the examples below.

EXAMPLES

Examples 1 to 4

Over a period of 7 hours, b mol of phosgene and c mol of hydrogen chloride were introduced at 140° C. into a mixture of 3 mol of gamma-butyrolactone and 0.02 mol of the urea compound III ($R^2$, $R^3$=$CH_3$, Z is variable). After the reaction had ended, the reaction mixture was freed of excess phosgene and hydrogen chloride by passing through nitrogen at about 80° C., and the mixture was analyzed by gas chromatography. The details of Examples 1 to 4 and their results are shown in Table 1 below.

Example 5

Over a period of 7 hours, b mol of thionyl chloride were added dropwise and c mol of hydrogen chloride gas were introduced at 140° C. into a mixture of 3 mol of lactone II and 0.02 mol of dimethylpropyleneurea. After the reaction had ended, the reaction mixture was freed of excess hydrogen chloride by passing through nitrogen at about 80° C., and the mixture was analyzed by gas chromatography. The details of Example 5 and its result are shown in Table 1 below.

TABLE 1

| Example | Lactone II | Urea compound | Chlorinating agent b [mol] | HCL c [mol] | GC analysis [%] Chlorocarbonyl chloride I | Lactone II | Chlorocarboxylic anhydride |
|---|---|---|---|---|---|---|---|
| 1 | gamma-Butyrolactone | Dimethylpropyleneurea | $COCl_2$/1.05 | 0.1 | 94.4 | 2.2 | 0.1 |
| 2 | gamma-Butyrolactone | 1) | $COCl_2$/1.05 | 0.1 | 91.7 | 2.9 | 0.2 |
| 3 | gamma-Butyrolactone | Dimethylethyleneurea | $COCl_2$/1.05 | 0.1 | 91.6 | 1.3 | 0.4 |
| 4 | gamma-Butyrolactone | Tetrabutylurea | $COCl_2$/1.05 | 0.1 | 86.2 | 6.9 | 0.2 |
| 5 | gamma-Butyrolactone | Dimethylpropyleneurea | $SOCl_2$/1.05 | 0.1 | 83.9 | 9.7 | 2.7 |

1) Dimethylpropyleneurea, as distillation residue of Example 1.

We claim:

1. A process for preparing chlorocarbonyl chlorides of the formula I $$R^1\text{—CHCl—Y—COCl} \qquad (I),$$

where $R^1$ is hydrogen, or is $C_1$- to $C_{20}$-alkyl, $C_2$- to $C_{12}$-alkenyl, $C_2$- to $C_{12}$-alkynyl, each of which is unsubstituted or mono- to trisubstituted by $C_1$- to $C_4$-alkoxy, $C_2$- to $C_4$-acyl, $C_2$- to $C_4$-acyloxy, $C_2$- to $C_8$-dialkylamino, halogen, nitro and/or cyano, or is $C_3$- to $C_{12}$-cycloalkyl, $C_4$- to $C_{12}$-alkylcycloalkyl, $C_4$- to $C_{12}$-cycloalkylalkyl, heterocycloalkyl, $C_5$- to $C_{20}$-heterocycloalkylalkyl, $C_6$- to $C_{14}$-aryl, $C_7$- to $C_{20}$-arylalkyl or $C_7$- to $C_{20}$-alkylaryl, each of which is unsubstituted or mono- to trisubstituted by $C_1$- to $C_4$-alkyl, $C_1$- to $C_4$-alkoxy, $C_2$- to $C_4$-acyl, $C_2$- to $C_4$-acyloxy, $C_2$- to $C_8$-dialkylamino, halogen, nitro and/or cyano, and Y is a saturated or mono- or polyolefinically unsaturated $C_2$–$C_8$-alkylene chain which may be interrupted by an ether, thioether, tertiary amino, keto, lactone, N-alkylsubstituted lactam or sulfone group and is unsubstituted or mono- to trisubstituted by $C_1$- to $C_4$-alkyl, $C_1$- to $C_4$-alkoxy, $C_2$–$C_4$-acyl, $C_2$–$C_4$-acyloxy, $C_2$–$C_8$-dialkylamino, halogen, nitro and cyano, by reacting the lactone of the formula II

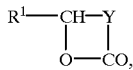

(II)

where $R^1$ and Y are each as defined above, with phosgene in the presence of a urea compound of the formula III

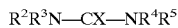

where the radicals $R^2$, $R^3$, $R^4$ and $R^5$ may be identical or different and, independently of the others, each has the meanings given for $R^1$ with the exception of hydrogen, or where one of the radicals $R^2$ or $R^3$ together with one of the radicals $R^4$ or $R^5$ are a hydrocarbon chain having 2 to 8 carbon atoms which may contain an ether, thioether, tertiary amino, keto, lactone, alkyl-substituted lactam, sulfone or diketo group and which is saturated or mono- or polyolefinically unsaturated and is unsubstituted or mono- to trisubstituted by $C_1$–$C_4$-alkyl, $C_1$–$C_4$-alkoxy, $C_2$–$C_4$-acyl, $C_2$–$C_4$-acyloxy, phenoxy, $C_2$–$C_8$-ciialkylamino, halogen, nitro and cyano, or are a cycloalkylene group having 5 to 12 carbon atoms, a heterocycloalkylene group having 4 to 11 carbon atoms, an arylene group having 6 to 12 carbon atoms or a heteroarylene group having 3 to 11 carbon atoms, each of which is unsubstituted or mono- to trisubstituted by $C_1$–$C_4$-alkyl, $C_1$–$C_4$-alkoxy, phenoxy, $C_2$–$C_4$-acyl, $C_2$–$C_4$-acyloxy, $C_2$–$C_8$-dialkylamino, halogen, nitro and/or cyano, and where X is an oxygen or sulfur atom, and/or a urea compound of the formula IV

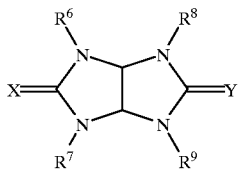

(IV)

where X is as defined above, $R^6$, $R^7$, R8 and $R^9$ may be identical or different and, independently of the others, each has the meanings given for $R^1$, with the exception of hydrogen, and/or a compound of the formula (V),

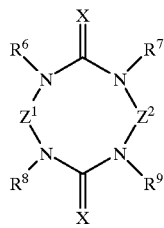

(V)

where X, $R^6$ to $R^9$ are each as defined above and $Z^1$, $Z^2$, which may be identical or different, are a methylene, ethylene or vinylene group which is unsubstituted or mono- to trisubstituted by $C_1$–$C_4$-alkyl, $C_1$–$C_4$-alkoxy, $C_2$–$C_4$-acyl, $C_2$–$C_4$-acyloxy, phenoxy, $C_2$–$C_8$-dialkylamino, halogen, nitro and/or cyano.

2. A process for preparing chlorocarbonyl chlorides as claimed in claim 1, wherein N,N-dimethylethyleneurea, N,N'-dimethylpropyleneurea, N,N'-tetrabutylurea, N,N'-tetramethylthiourea, N-chloromethyl-N'-cyanomethylpropyleneurea, N-methyl-N'-ethylpropyleneurea, 1,3-dimethyl-1,3-dihydrobenzimidazol-2-one, 1-methyl-3-phenylimidazolidine-2,4,5-trione, 1,3,4,6-tetramethyl-1,3,4,6-tetrahydroimidazo[4,5-D]imidazole-2,5-dione and 4-methoxy-1-methyl-3-phenylimidazolidine-2-thione are employed.

3. A process for preparing chlorocarbonyl chlorides as claimed in claim 1 wherein the urea compound is employed in a molar ratio of from 0.001:1 to 0.2:1 relative to the lactone II.

4. A process for preparing chlorocarbonyl chlorides as claimed in claim 1, wherein phosgene is employed in a molar ratio of from 0.5:1 to 50:1 relative to the lactone II.

5. A process for preparing chlorocarbonyl chlorides as claimed in claim 1, wherein the reaction is carried out in the presence of hydrogen chloride.

6. A process for preparing chlorocarbonyl chlorides as claimed in claim 1, wherein the reaction is carried out at from -20 to 180° C.

* * * * *

UNITED STATES PATENT AND TRADEMARK OFFICE
CERTIFICATE OF CORRECTION

| | |
|---|---|
| PATENT NO. | : 6,262,300 B1 |
| DATED | : July 17, 2001 |
| INVENTOR(S) | : Weyer et al. |

Page 1 of 1

It is certified that error appears in the above-identified patent and that said Letters Patent is hereby corrected as shown below:

<u>Column 7, claim 1,</u>
Line 23, "$C_2$-$C_8$-ciialkylamino" should be -- $C_2$-$C_8$-dialkylamino --.
Line 44, "R8" should be -- $R_8$ --.

Signed and Sealed this

Nineteenth Day of March, 2002

Attest:

JAMES E. ROGAN
*Director of the United States Patent and Trademark Office*

*Attesting Officer*